United States Patent
Castorena Cortes et al.

(10) Patent No.: US 10,287,484 B2
(45) Date of Patent: May 14, 2019

(54) **PROCESS FOR RECOVERY AND MOBILIZATION OF OIL CONTAINED IN POROUS MEDIA BY TENSOACTIVE BIOMOLECULES PRODUCED BY *SERRATIA MARCESCENS* SMSA**

(71) Applicant: INSTITUTO MEXICANO DEL PETRÓLEO, Mexico City (MX)

(72) Inventors: Gladys Teresa Castorena Cortes, Mexico City (MX); Teresa Guadalupe Roldan Carrillo, Mexico City (MX); Patricia Olguin Lora, Mexico City (MX)

(73) Assignee: INSTITUTO MEXICANO DEL PETROLEO, Mexico City (MX)

(*) Notice: Subject to any disclaimer, the term of this patent is extended or adjusted under 35 U.S.C. 154(b) by 0 days.

(21) Appl. No.: 15/719,828

(22) Filed: Sep. 29, 2017

(65) Prior Publication Data
US 2018/0094184 A1 Apr. 5, 2018

(30) Foreign Application Priority Data
Sep. 30, 2016 (MX) .................. A/2016/012847

(51) Int. Cl.
*C09K 8/584* (2006.01)
*C09K 8/582* (2006.01)
(Continued)

(52) U.S. Cl.
CPC ............. *C09K 8/584* (2013.01); *C09K 8/582* (2013.01); *C12N 1/20* (2013.01); *C12P 1/04* (2013.01);
(Continued)

(58) Field of Classification Search
CPC ................................................. E21B 43/22
See application file for complete search history.

(56) References Cited

U.S. PATENT DOCUMENTS 4,522,261 A * 6/1985 McInerney ............ C09K 8/905
166/246

OTHER PUBLICATIONS

Ferraz et al. (Evaluation of the effect of nutrient ratios on biosurfactant prodiction by Serratoa marcescens, 2011).*

(Continued)

*Primary Examiner* — Angela M DiTrani Leff
*Assistant Examiner* — Avi T Skaist
(74) *Attorney, Agent, or Firm* — Dickinson Wright PLLC

(57) ABSTRACT

The present invention is related with a biotechnological process that increases the recovery and mobilization of oils present in carbonated and/or siliciclastic porous media by the action of tensoactive biomolecules from *Serratia marcescens* SmSA.

The invention also increases the oil recovery in reservoirs. *Serratia marcescens* SmSA biomolecules display tensoactive and emulsifying properties that produce changes in the surface and interfacial tensions, enhanced the recovery and mobilization of oils.

The *Serratia marcescens* SmSA tensoactive biomolecules of the present invention are stable at temperatures from 4 to 121° C., pH from 2 to 12, pressures from atmospheric to 1,706 psi, and NaCl content from 0 to 200 g/L (from 0 to 200,000 ppm).

The *Serratia marcescens* SmSA tensoactive biomolecules reduce the surface tension up to 26 mN/m, the interfacial tension up to 1.8 mN/m with hexadecane, with emulsifying activity up to 71% with the same solvent and a critical micellar concentration (CMC) of 300 mg/L.

The *Serratia marcescens* SmSA tensoactive biomolecules enhance recovery of residual oil above 10%.

9 Claims, 5 Drawing Sheets

(51) Int. Cl.
    *C12P 1/04* (2006.01)
    *C12R 1/43* (2006.01)
    *E21B 43/16* (2006.01)
    *C12N 1/20* (2006.01)
    *E21B 43/20* (2006.01)
    *E21B 49/00* (2006.01)
    *E21B 49/08* (2006.01)

(52) U.S. Cl.
    CPC ............... *C12R 1/43* (2013.01); *E21B 43/16* (2013.01); *E21B 43/20* (2013.01); *E21B 49/00* (2013.01); *E21B 49/08* (2013.01)

(56) References Cited

OTHER PUBLICATIONS

Ibrahim et al. (Production and partial characterization of biosurfactant produced by crude oil degrading bacteria, 2013).*

Roldan-Carrillo et al. (Evaluation of the effect of nutrient ratios on biosurfactant production by Serratia marcescens using a Box-Behnken design, 2011).*

\* cited by examiner

PROCESS FOR RECOVERY AND MOBILIZATION OF OIL CONTAINED IN POROUS MEDIA BY TENSOACTIVE BIOMOLECULES PRODUCED BY *SERRATIA MARCESCENS* SMSA

CROSS REFERENCE TO RELATED APPLICATIONS

This application claims the benefit of Mexican Priority Patent Application MX/a/2016/012847 filed Sep. 30, 2016, the entire contents of which are incorporated herein by reference.

TECHNICAL FIELD

The present invention related to a biotechnological process that increases the recovery and mobilization of oils contained in carbonated and/or siliciclastic porous media by tensoactive biomolecules produced by *Serratia marcescens* SmSA strain. The present invention also increases the oil recovery in reservoirs. The invention also features the production process of the tensoactive biomolecules by *Serratia marcescens* SmSA

BACKGROUND

The oil recovery processes are known as primary, secondary and tertiary or enhanced recovery processes.

The primary recovery of oil takes place when the fluids flow toward the wells is the result of the natural energy present in the reservoir.

The secondary recovery takes place when energy is added to the reservoir by the injection of an immiscible fluid, keeping or restarting the displacement of oil toward the well production.

The enhanced or tertiary recovery of oil, "Enhanced Oil Recovery" (EOR), is the application of processes that produce an additional oil recovery, where the injection of a fluid into the reservoir modifies the original characteristics of the rock and/or the fluids involved in the displacement by reducing the oil viscosity, modifying the behavior of the phases, reducing the interface tension, etc.

Among the EOR processes, the microbial recovery of hydrocarbons is found, "Microbial Enhanced Oil Recovery" (MEOR), which can be put into practice by three strategies:
1) Inducing selectively the growth and metabolic activity of indigenous microorganisms present in the reservoirs, through the injection of nutrients and carbon sources that favor the microbial activity to produce metabolites such as $CO_2$, $CH_4$, solvents, acids and tensoactive biomolecules (biosurfactants), that are useful for the mobilization, and therefore, the oil recovery from the reservoirs.
2) Adding exogenous microorganisms capable of producing useful metabolites for the recovery of oil.
3) Applying bioproducts such as tensoactive biomolecules, enzymes, acids, biopolymers among others, that improve the reservoir conditions and favor the release of oil.

Most patents on microbial enhanced oil recovery imply the injection of microorganisms or the selective stimulation of reservoir indigenous microorganisms. The aim is to make the microorganisms grow to produce compounds such as gases, biosurfactants or solvents, that modify the properties of the oil and allow its mobilization. These compounds are produced in situ and depend on suitable environmental and nutritional conditions for the development of such microorganisms.

On the other hand, many of the strains that produce tensoactive biomolecules require aerobic conditions for their growth. However, most of these microorganisms cannot withstand both high temperatures and salt concentrations.

In the patent application WO2009009382 "Process for enhanced oil recovery using a microbial consortium", published on Jan. 15, 2009, a process for the selection and enrichment of microorganisms, where the nutritional components to propagate the microbial growth is defined. The culture medium and microorganisms were injected into the well, which was closed up to 3 weeks to allow the development of the microorganisms, the production of metabolites and the oil recovery.

In the patent application US 2009/0029879 A1 "Process for enhanced oil recovery using a microbial consortium", published on Jan. 29, 2009, Soni et al. describe a microbial consortium that was injected along with a culture medium designed for its growth. The metabolic products increased the oil recovery. The consortium was able to grow a temperature of 67° C.

Tensoactive biomolecules are a heterogeneous group of amphiphilic compounds with tensoactive properties. These compounds feature a variety of chemical structures and many of them are produced by microorganisms.

Tensoactive biomolecules have high surface activity and are stable within a wide interval of temperatures, pH and salinity, in addition to be biodegradable and less toxic than chemical surfactants. These biomolecules reduce the surface tension (ST) and the interfacial tension (IFT), easing the formation of emulsions. Some of their potential applications include the improvement of the mobility of oils, the enhanced oil recovery by microorganism (MEOR) and the hydrocarbons biodegradation by increasing the bioavailability of hydrophobic compounds.

These compounds can improve some properties of oils, such as the decrease of the surface and interfacial tensions and the reduction of oil viscosity to make it more fluid. Among patent documents on tensoactive biomolecules applied in EOR, the following are found:

The patent U.S. Pat. No. 4,522,261 "Biosurfactant and enhanced oil recovery", from Jun. 11, 1985, where McInerney et al. propose a process for increasing the oil recovery from reservoirs by a pure culture of Bacillus licheniformis and the lichenysin surfactant that is produced. The obtained results and the claimed subject are based on oil recovery experiments performed in glass column systems, packed with quartz sand impregnated with crude oil. The characteristics of the employed oil are not stated; the columns were kept at 25° C., under different conditions from those in the reservoir and with only qualitative oil recovery results. The characteristics and culture conditions of the microorganism *B. licheniformis* are very different from those used with the microorganism *Serratia marcescens* SmSA featured in the present invention.

Hames et al. (2015: Patents on biosurfactants and future trends. Chapter 11. In: BIOSURFACTANTS Production and Utilization-Processes, Technologies, and Economics, Edited by Kosaric N. and Sukan F. V., CRC Press Taylor & Francis Group, Boca Raton London New York, FL. 165-225) present a wide review of patents on the production of biosurfactants and their application, including the recovery of reservoir oils. This review covered up to 2013 and the authors show that the main microorganisms that produce biosurfactants belong mainly to: *Acinetobacter,*

Bacillus, Pseudomonas, Torulopsis and Candida genus. Among the patents reviewed in this study regarding the use of Serratia marcescens, none considered neither its application in the production of biomolecules with tensoactive activity nor its use in some biotechnological process for oil recovery.

In "novel sucrose lipid produced by Serratia marcescens and its application in enhanced oil recovery", Journal of Surfactants and Detergents, Vol. 3, No. 4 (October 2000), pp. 533-537, Vikas Pruthi and Swaranjit S. Cameotra reported that Serratia marcesens cultivated in a medium with sucrose at 2% (p/v) produced a saccharolipid with emulsifying properties. With this compound, recovery tests were carried out, employing glass columns, packed with sand saturated with oil; the results were 78% of crude oil recovery and 90% of kerosene. The conditions (temperature and oil type) under which the experiment was carried out are not stated.

Roldan et al. in "Evaluation of the effect of nutrient ratios on biosurfactant production by Serratia marcescens using a Box-Behnken design", Colloids and Surfaces B: Biointerfaces 86 (2011), pp. 384-389, study the microorganism Serratia marcescens and the effect of the C/N, C/Fe and C/Mg ratios on the production of biosurfactants using glucose as carbon source by a Box-Behnken experiment design. With the best treatment, a yield of 4.1 g/L of biosurfactant was obtained, which diminished the surface tension to 31 mN/m and produced maximum oil spreading of 1.1 cm.

Ibrahim et al. in "Production and partial characterization of biosurfactant produced by crude oil degrading bacteria", International Biodeterioration & Biodegradation 81 (2013), pp. 28-34, report the isolation of several biosurfactant producer microorganisms using a mineral medium, where the substrate was crude oil. Among the evaluated microorganisms, Serratia marcescens and its produced biosurfactant were reported. The biosurfactant was used for oil recovery experiments in packed columns. With these experiments, 30% oil recovery was obtained by waterflooding and 46% by the biosurfactant action, with a total oil recovery of 76%. The authors do not mention the conditions under which the column recovery experiment was carried out, the type of rock, the oil characteristics and temperature.

In the previous references, the recovery of oil by tensoactive biomolecules were performed in columns packed with siliciclastic rocks, which are porous media with high permeability. In addition, these reports lack of fundamental information for the studies on the oil recovery such as pressure, temperature, API gravity and oil viscosity.

1) Sampling and characterization of fluids and rocks from the oil well.
2) Isolation of the microorganisms that produce tensoactive biomolecules.
3) Molecular identification of the microorganisms that produce tensoactive biomolecules.
4) Formulation of the culture medium for the production of biomolecules with tensoactive properties by Serratia marcescens SmSA.
5) Optimization of the production of biomolecules with tensoactive properties by Serratia marcescens SmSA
6) Production of biomolecules with tensoactive properties by Serratia marcescens SmSA at reactor level.
7) Evaluation of the activity and stability of biomolecules with tensoactive properties by Serratia marcescens SmSA.
8) Oil recovery in unconsolidated systems (granular porous media).
9) Oil recovery in consolidated systems (core).

Figure 2:
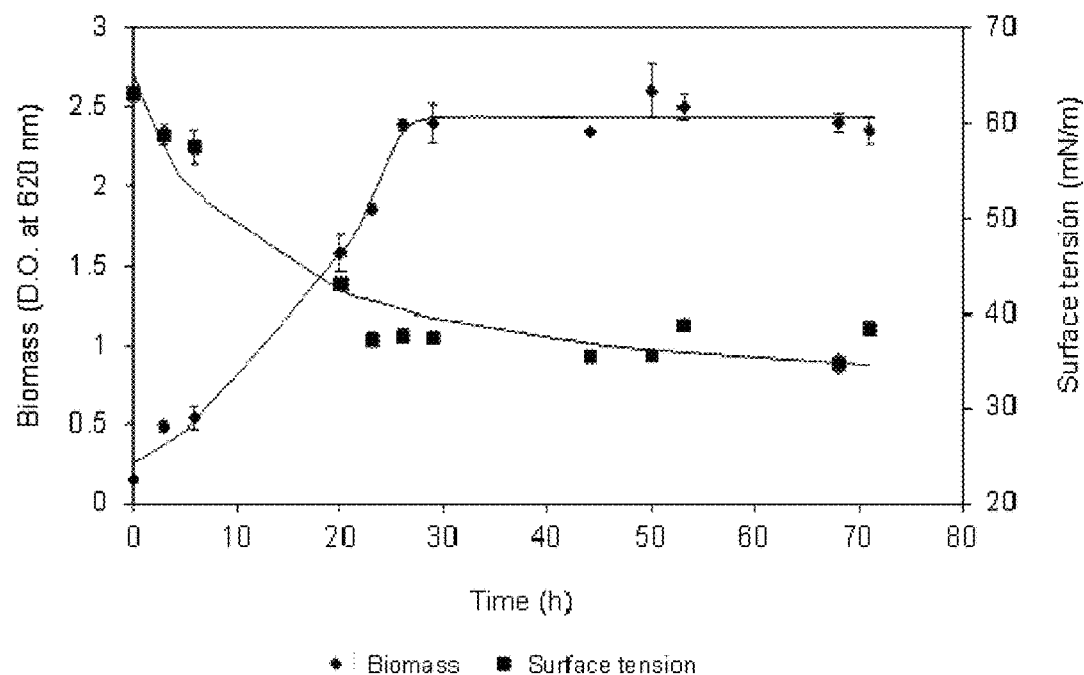

FIG. 2 shows the evaluation of the growth of Serratia marcescens SmSA strain at 30° C. with soybean oil as substrate, and the evaluation of production of tensoactive molecules through surface tension reduction.

Figure 3:
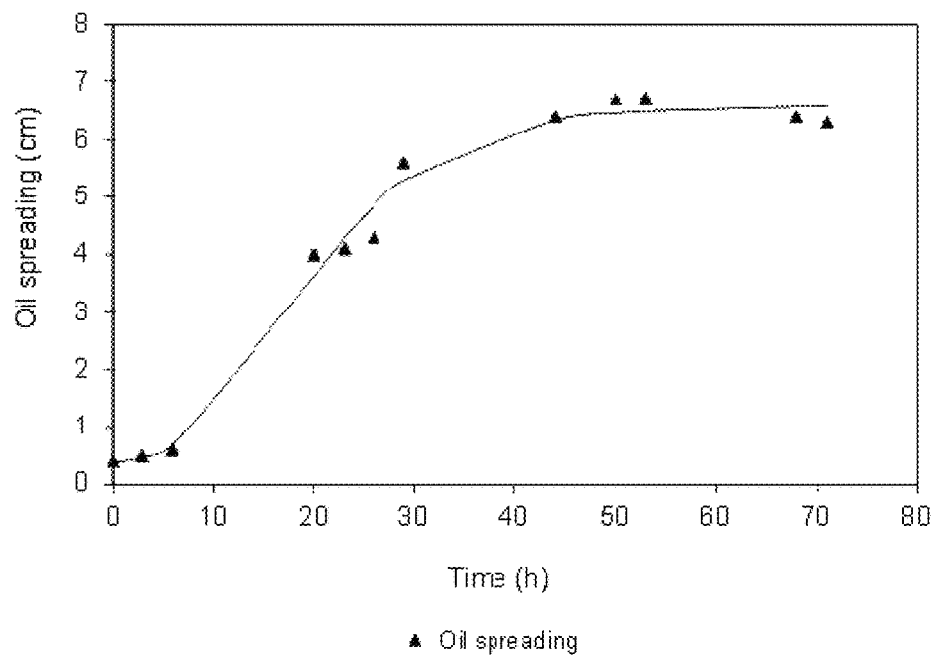

FIG. 3 shows the evaluation of the production of tensoactive biomolecules by oil spreading by Serratia marcescens SmSA strain at 30° C. with soybean oil as substrate.

Figure 4:
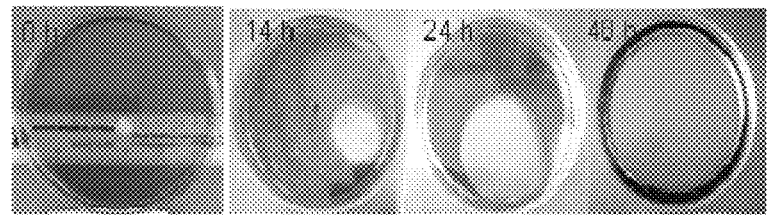

FIG. 4 shows the evolution oil spreading by Serratia marcescens SmSA biomolecules with soybean oil as substrate.

Figure 5:
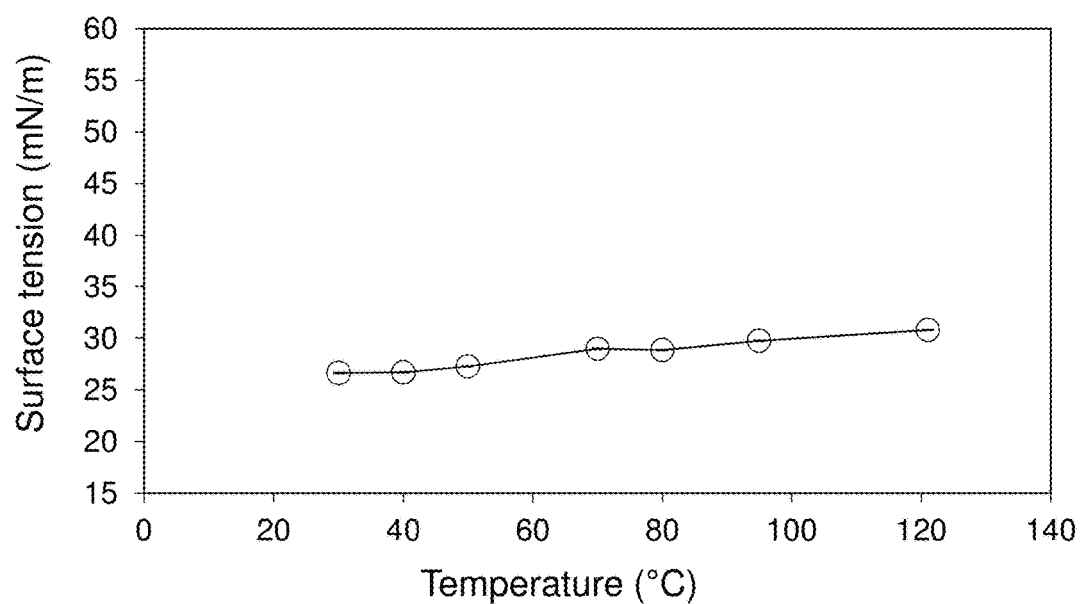

FIG. 5 shows the stability of Serratia marcescens SmSA tensoactive biomolecules at different temperatures.

Figure 6:
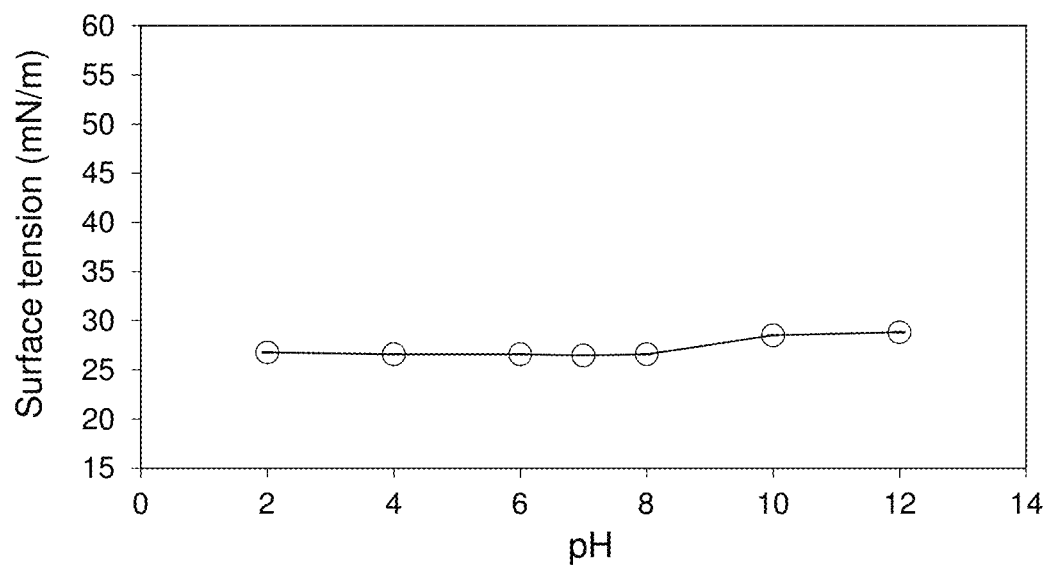

FIG. 6 illustrates the stability of Serratia marcescens SmSA tensoactive biomolecules at different pH conditions.

Figure 7:
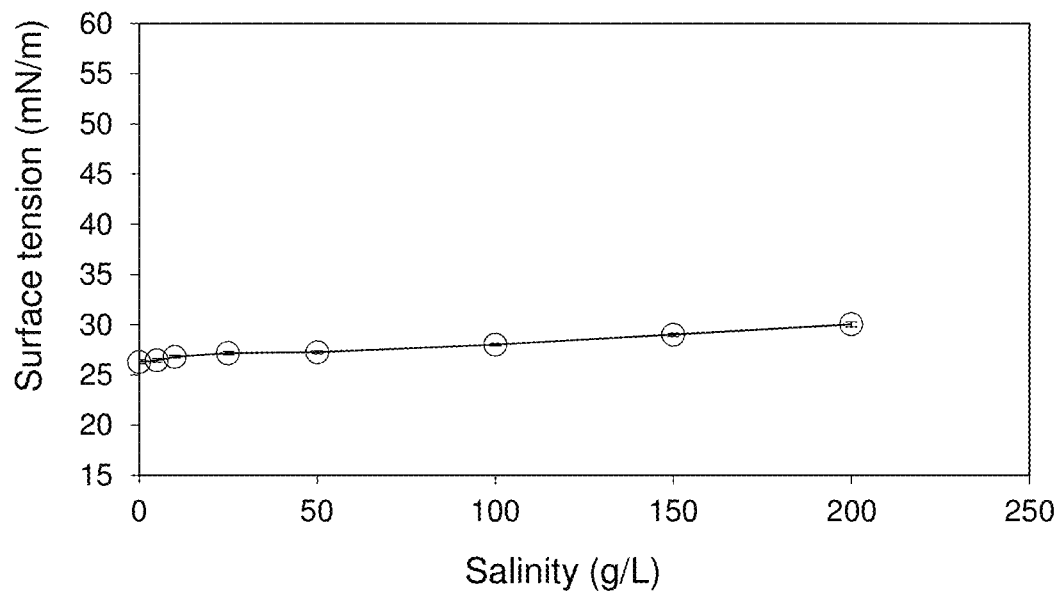

FIG. 7 shows the stability of Serratia marcescens SmSA tensoactive biomolecules at different salinity concentrations (NaCl).

Figure 8:
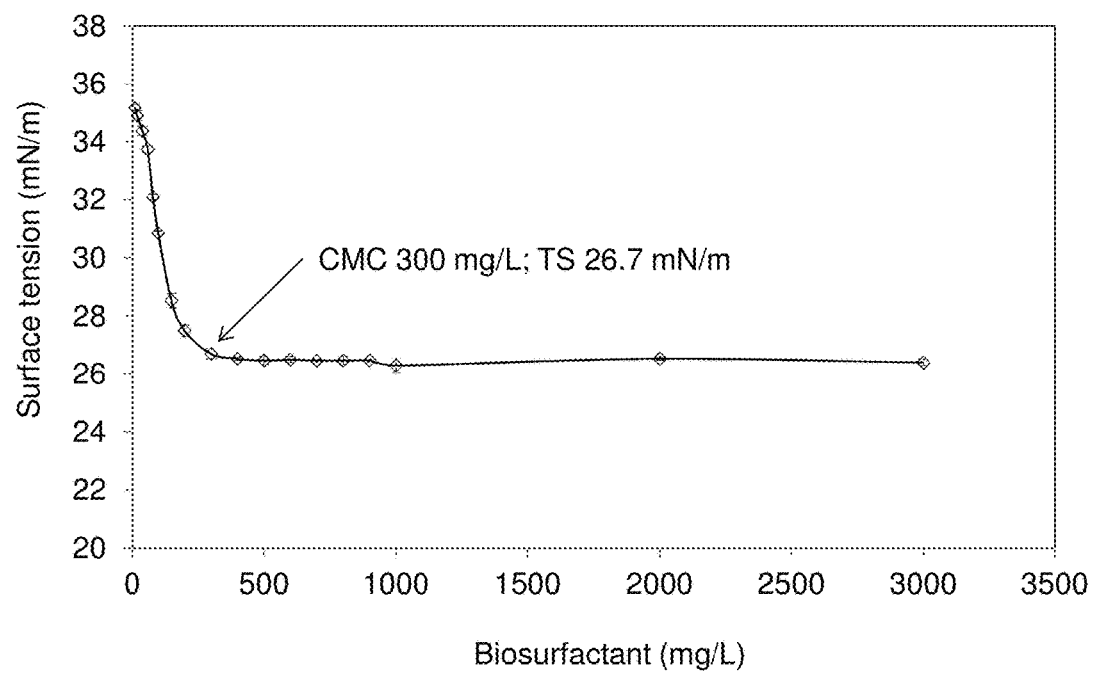

FIG. 8 shows the determination of the critical micellar concentration (CMC) of Serratia marcescens SmSA tensoactive biomolecules.

DETAILED DESCRIPTION OF INVENTION

The present invention refers to a biotechnological process that increases the recovery and mobilization of oils contained in carbonated and/or siliciclastic porous media by Serratia marcescens SmSA biomolecules with tensoactive properties. The present invention also increases the oil recovery in reservoirs. It is important to point out that Serratia marcescens biomolecules display tensoactive and emulsifying properties that produce changes in the surface and interfacial tensions, increasing the mobilization and recovery of oils.

Serratia marcescens biomolecules with tensoactive properties featured in the present invention are stable at temperatures ranging from 0 to 120° C., pH from 2 to 12, pressures from atmospheric to 1,706 psi and NaCl content from 0 to 200 g/L (0 to 200,000 ppm).

Serratia marcescens SmSA biomolecules reduce the surface tension up to 26 mN/m, the interfacial tension up to 1.8 mN/m with hexadecane, have emulsifying activity up to 71% with the same solvent, and a critical micellar concentration (CMC) of 300 mg/L.

Figure 1:
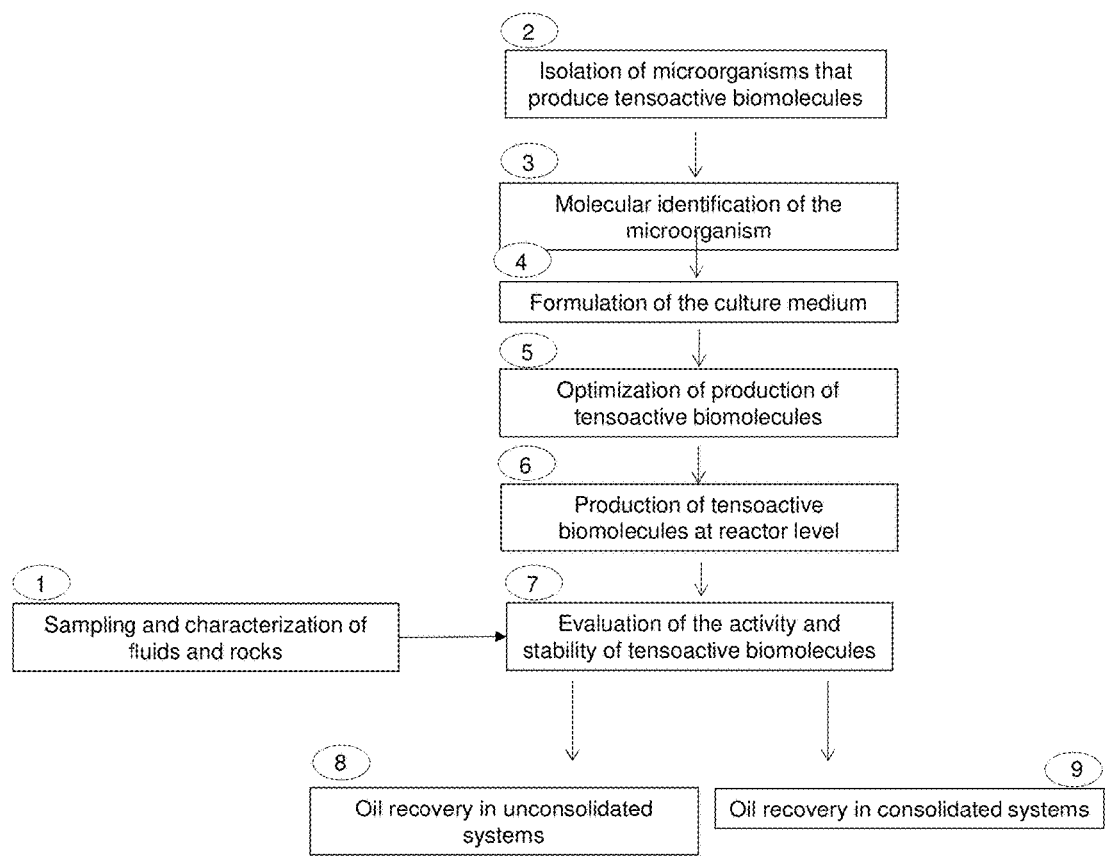
FIG. 1 shows, through a flow chart, the different stages that were developed to obtain the biotechnological process featured in this invention.

In order to help understand better the invention, FIG. 1 shows, through a flow chart, the different stages that were developed to obtain the biotechnological process featured in the present invention:

1) Sampling and characterization of fluids and rocks from the oil well.—It consists in obtained samples rock and fluid (oil and water) from the oil well in order to characterization and determination of:
   Oil API gravity,
   Type of porous media: siliciclastic and/or carbonated,
   Porosity and permeability of the porous media, and
   Conditions of the oil well: temperature, pressure and salinity.

The oil well must have one or more of the following properties, which increase the success possibilities of the recovery process: type of porous medium (siliciclastic and/or carbonated), porosity ≥15%, permeability >20 mD, oil °API gravity >15, temperature of reservoir up to 120° C., and formation water salinity up to 200,000 ppm.

2) Isolation of the microorganisms that produce tensoactive biomolecules.—It consists in obtaining samples of petroleum environments to isolate microorganisms that produce tensoactive biomolecules.

The isolation consists in obtained a contaminated soil sample with oil and placing it in a suitable culture medium, like the mineral media shown in Tables 1 and 2 with different substrates (glycerol, hexadecane and eicosane), in order to develop microorganisms and evidence the production of tensoactive biomolecules.

TABLE 1

Formulation of the mineral medium.

| Compound | (g/L) |
| --- | --- |
| $KH_2PO_4$ | 0.3-0.7 |
| $K_2HPO_4$ | 1.3-1.9 |
| $NH_4Cl$ | 1.1-1.7 |
| $MgCl_2\ 6H_2O$ | 0.05-0.3 |
| $NaSO_4\ 7H_2O$ | 0.5-1.0 |
| $CaCl_2\ 2H_2O$ | 0.03-0.06 |
| Solution of trace elements | 0.5-2.0 mL/L |
| Substrate * | 5-10 mL/L ó 5-10 g/L |

* Glycerol, hexadecane or eicosane.
Culture medium pH of 6-7.

TABLE 2

Formulation of the trace element solution.

| Compound | (g/L) |
| --- | --- |
| $MnCl_2\ 2H_2O$ | 0.4-0.8 |
| NaCl | 0.5-1.2 |
| $FeCl_3\ 6H_2O$ | 0.5-1.0 |
| $CuCl_2$ | 0.01-0.15 |
| $ZnCl_2$ | 0.04-0.1 |
| $AlCl_3$ | 0.025-0.05 |
| $H_3BO_3$ | 0.005-0.01 |
| $Na_2MoO_4\ 2H_2O$ | 0.02-0.06 |

The isolated microorganisms are evaluated according to their production capacity of tensoactive biomolecules by the oil spreading technique (Noha H. Youssef et al. "Comparison of methods to detect biosurfactant production by diverse microorganisms", Journal of Microbiological Methods 56 (2004) 339-347) and emulsifying activity (Gizele Cardoso Fontes et aL, "Factorial Design to Optimize Biosurfactant Production by Yarrowia lipolytica", Journal of Biomedicine and Biotechnology Volume 2010, Article ID 821306, 8 pages).

The evaluation of tensoactive biomolecules production is carried out with the cell-free supernatant from isolated microorganisms cultures. At this stage, the microorganisms with the highest tensoactive activity are selected.

From the soil samples, 13 strains were isolated in nutrient broth and mineral medium with hydrocarbons as carbon source (Tables 1 and 2).

The isolated strains were evaluated by oil spreading and emulsifying activity techniques in order to explore their capacity to produce tensoactive biomolecules. The microbial cultures were incubated at 30° C. with stirring at 115 rpm for 7 days. The determination of the oil spreading and emulsifying activity ($E_{24}$) indicated that the best strain was denominated SmSA, because the tensoactive biomolecules that it produced were capable of dispersing oil of 0.7-0.8 cm. The emulsifying activity with kerosene was 41-62%.

3) Molecular identification of the microorganism with the best production of tensoactive biomolecules.—It consists in characterizing the SmSA strain selected for its tensoactive activity at Stage 2 by biochemical tests and molecular techniques to establish its genus and species.

In this sense, the SmSA strain was identified by biochemical and molecular biology techniques. The isolated bacterium was identified biochemically with the diagnostic test API 20E (bioMerieux). Its metabolic profile corresponded to the Enterobacteraceae family and the *Serratia* genus. The sequence analysis of the 16S rRNA gen indicated that the SmSA strain belongs to *Serratia marcescens* with 99.7% of similitude.

The sequence obtained with the SmSA strain was registered in the GenBank database with the Access number HQ686060.

The SmSA strain identified as *Serratia marcescens* was deposited on Collection of Microorganisms of the National Center of Genetic Resources, Mexico, (CM-CNRG), with the registration number CM-CNRG TB20, for the purposes regarding the processing of patents according to the Budapest Treaty on the international recognition of the deposit of microorganisms.

The microorganism *Serratia marcescens* SmSA, producer of tensoactive biomolecules, was preserved under freezing at −70° C. in a cryogenic vial with glycerol at 20%.

4) Formulation of the culture medium for the production of biomolecules with tensoactive properties by *Serratia marcescens* SmSA.—It consists in formulating the culture medium with the necessary and suitable nutrients for improving the production of tensoactive biomolecules by *Serratia marcescens* SmSA microorganism, which was selected as the best producer of these metabolites for its highest tensoactive activity at Stage 2.

The formulation of nutrients to improve the production of tensoactive biomolecules with the microorganism selected at Stage 2, *Serratia marcescens* SmSa, consisted of the compounds featured in Table 3 and different substrates used as carbon sources:

glucose, sucrose, molasses, glycerol, hexadecane and soybean oil, preferably at concentrations from 5 to 15 g/L or from 5 to 15 mL/L. The cultures were incubated at temperatures from 25 to 37° C., with stirring from 100 to 150 rpm for 48 h.

TABLE 3

Composition of the culture medium for the production of tensoactive biomolecules by *Serratia marcescens* SmSA

| Compound | (g/L) |
| --- | --- |
| Peptone | 2-6 |
| $K_2HPO_4$ | 10-15 |
| $KH_2PO_4$ | 8-18 |
| $(NH_4)_2SO_4$ | 0.5-4.0 |
| pH | 6-8 |

The selection of the best substrate for the production of tensoactive biomolecules was carried out by evaluating the growth of the selected microorganism and the production of tensoactive biomolecules through the surface tension and oil spreading technique.

The results in Table 4 show that the best substrates for the production of tensoactive biomolecules were hexadecane, soybean oil and sucrose, which provided better growth rates than the other carbon sources with surface tension reductions of 30, 29.5 and 32.3 mN/m and oil dispersion halos of 2.4, 7.4 and 1.15 cm, respectively. Although, with hexadecane and soybean oil, these values were obtained approximately after 24 h and with sucrose after 48 h.

TABLE 4

Evaluation of the growth and production of tensoactive biomolecules by *Serratia marcescens* SmSA with different carbon sources.

| Carbon Source | Biomass (DO a 620 nm) | | | Oil spreading (cm) Time (h) | | | Surface Tension (mN/m) | | |
|---|---|---|---|---|---|---|---|---|---|
| | 0 | 24 | 48 | 0 | 24 | 48 | 0 | 24 | 48 |
| Glycerol | 0.33 | 0.61 | 0.74 | 0.6 | 0.6 | 0.9 | 68.0 | 65.0 | 68.0 |
| Hexadecane | 0.05 | 1.90 | 1.84 | 1.0 | 1.6 | 2.4 | 55.0 | 27.0 | 25.0 |
| Sucrose | 0.12 | 0.75 | 1.41 | 0.35 | 0.4 | 1.15 | 57.3 | 39.8 | 25.0 |
| Molasses | 0.07 | 0.18 | 0.19 | 0.3 | 0.4 | 0.4 | 68.0 | 61.0 | 61.0 |
| Glucose | 0.09 | 0.73 | 0.99 | 0.6 | 0.7 | 0.9 | 61.5 | 55.0 | 46.0 |
| Soybean oil | 0.13 | 0.89 | 1.32 | 0.60 | 6.1 | 7.4 | 55.5 | 26.8 | 26.0 |

OD: Optical Density.

Soybean oil was one of the best substrates evaluated in the production of tensoactive biomolecules by *Serratia marcescens* SmSA, and therefore it was selected for a kinetic study with this substrate.

The maximum reduction of the surface tension was of 26.5 mN/m and presented an oil spreading of 7.1 cm as shown in FIGS. 2 to 4.

5) Optimization of the production of tensoactive biomolecules by *Serratia marcescens* SmSA.—It consists in optimizing the formulation of the culture medium for the production of tensoactive biomolecules by *Serratia marcescens* SmSA, through a Taguchi $L_9$ ($3^4$) experimental design, which allows the evaluation of 4 variables at 3 different levels.

The variables with their levels were:
Temperature: 25, 30 and 37° C.,
Carbon/Nitrogen (C/N) ratio: 6, 12 and 18,
Agitation: 100, 150 and 200 rpm, and
Agitation/Temperature (A/T) ratio: 1, 2 and 3.
The experimental design was carried out:
Systems of 250-mL were prepared containing 100 mL of culture medium as shown in Table 3, where according to the Taguchi $L_9$ experimental design combinations of the different studied variables were performed as displayed in Table 5.

TABLE 5

Systems of experimental design for the production of tensoactive biomolecules by *Serratia marcescens* SmSa.

| System | Temperature (° C.) | Agitation (rpm) | C/N ratio | A/T ratio | ST (mN/m) | ST Reduction (mN/m) |
|---|---|---|---|---|---|---|
| 1 | 25 | 100 | 6 | 1 | 30 | 24 |
| 2 | 25 | 150 | 12 | 2 | 33 | 21 |
| 3 | 25 | 200 | 18 | 3 | 32.7 | 21.3 |
| 4 | 30 | 100 | 12 | 3 | 40.5 | 13.5 |
| 5 | 30 | 150 | 18 | 1 | 38.3 | 15.7 |
| 6 | 30 | 200 | 6 | 2 | 38.5 | 15.5 |
| 7 | 37 | 100 | 18 | 2 | 40.7 | 13.3 |
| 8 | 37 | 150 | 6 | 3 | 34.4 | 19.6 |
| 9 | 37 | 200 | 12 | 1 | 40.1 | 13.9 |

C/N: Carbon/Nitrogen.
A/T: Agitation/Temperature.
TS: Surface Tension.

The systems were inoculated with the *Serratia marcescens* SmSA strain in order to optimize the production of biomolecules with tensoactive activity.

Each system was evaluated in the production of tensoactive biomolecules through the surface tension measurement.

The surface tension results for each system were statistically analyzed to obtain the significant effect of the incubation temperature, agitation and carbon/nitrogen ratio. According to this analysis, the highest surface tension reduction was of 24 mN/m, which was obtained with system 1 (ST: 30 mN/m) from the experiment design as reported in Table 5.

The production of *Serratia marcescens* SmSa biomolecules with tensoactive properties was verified through the best experimental design conditions, where the surface tension was lower 26.74 mN/m.

6) Production of tensoactive biomolecules with *Serratia marcescens* SmSA at reactor level.—This stage consists in the production of tensoactive biomolecules with *Serratia marcescens* SmSA at reactor level employing the optimized medium from Stage 5, where the culture C/N ratio was 6 (system 1).

In this sense, 3 experiments were prepared in duplicate with the conditions stated in Table 6. In each reactor experiment, a temperature of 25° C., agitation of 100 rpm, and a C/N ratio of 6 were kept constant under different aeration conditions.

TABLE 6

Operation conditions of the reactors for the production of *Serratia marcescens* SmSA tensoactive biomolecules.

| Reactor | Condition | | | Surface | |
|---|---|---|---|---|---|
| | Temperature (° C.) | Agitation (rpm) | Aeration (mL/min) | Tension (mN/m) | Time (h) |
| 1 | 25 | 100 | 300 | 27.5 | 56 |
| 2 | 25 | 100 | 750 | 26 | 56 |
| 3 | 25 | 100 | 1,000 | 26 | 28 |

Surface tension measurements were carried out throughout time since the inoculation of the culture medium. The best condition was with an aeration rate of 1,000 mL/min, where the surface tension was of 26 mN/m at 28 h.

7) Evaluation of the activity and stability of *Serratia marcescens* SmSA tensoactive biomolecules.—It consists in evaluating the surface and interfacial tension besides emulsifying activity of *Serratia marcescens* SmSA tensoactive biomolecules under different conditions: temperatures from 25 to 120° C., pH from 2 to 12 and salinity from 0 to 200,000 ppm. In addition, the critical micellar concentration (CMC) of the tensoactive biomolecules was also established.

The application of the tensoactive molecules depends on their stability under different conditions such as temperature, salinity and pH; for this reason, it is important to evaluate the stability of the *Serratia marcescens* SmSA biomolecules to establish their application range.

FIG. 5 shows that temperature did not has a significant effect on of the surface tension by employing *Serratia marcescens* SmSA biomolecules with the evaluated interval from 25 to 120° C., indicating that *Serratia marcescens* SmSA tensoactive biomolecules are thermostable.

The effect of pH on the surface tension was established by adjusting the pH of the cell-free supernatant from 2 to 12 with HCl (2 N) and NaOH (2 N). The stability of *Serratia marcescens* SmSA tensoactive biomolecules with respect to pH is shown in FIG. 6, where it is observed that under the different evaluated pH conditions, both acid and alkaline, the surface tension is kept constant with slight alterations. The aforementioned indicates that *Serratia marcescens* SmSA biomolecules are stable within a wide pH interval. The statistical analysis and the comparison of means of the pH evaluation results, indicate that there were no significant differences with respect to the surface tension between the treatments with a significance level ($\alpha$) of 0.05.

FIG. 7 shows the stability of *Serratia marcescens* SmSA tensoactive biomolecules at different salt concentrations; the statistical analysis by comparison of means indicates that there were no significant differences ($\alpha$=0.05) with respect to the surface tension between the treatments. This result implies that *Serratia marcescens* SmSA biomolecules can be used within a wide interval of salinities, from 0 to 200 g/L of NaCl.

The critical micellar concentration (CMC) is the minimal concentration of biomolecules necessary to reduce the surface tension to its maximum value. The CMC is an important parameter to evaluate tensoactive compounds and establish the optimal concentration in practical applications.

*Serratia marcescens* SmSA tensoactive biomolecules present in the cell-free supernatant were partially extracted by lyophilization and using a chloroform/methanol (2:1 v/v) mixture.

The partially purified *Serratia marcescens* SmSA tensoactive biomolecules displayed a yield of 5.45 g/L. With this product, different dissolutions were carried out with distilled water to obtain solutions with different concentrations of biomolecules from 10 to 3,000 mg/L, to evaluate the surface tension (FIG. 8). The CMC was of 300 mg/L with a surface tension value of 26.7 mN/m.

Storage stability of *Serratia marcescens* SmSA tensoactive biomolecules by refrigeration.—Table 7 shows the activity of *Serratia marcescens* SmSA tensoactive biomolecules preserved at 4° C. as a function of time. The results show that the biomolecules keep their tensoactive and emulsifying activities for several days.

TABLE 7

Assessment of the storage stability at 4° C. of *Serratia marcescens* SmSA tensoactive biomolecules

| Storage time (h) | Oil spreading (cm) | Surface Tension (mN/m) | Interfacial Tension (mN/m) | Emulsifying Activity, $E_{24}$ (%) |
|---|---|---|---|---|
| 0 | 7.5 | 26.5 | 9.5 | 71.1 |
| 24 | 6.5 | 26.5 | 9.5 | 71.1 |
| 48 | 5.4 | 28.3 | 11 | 69.62 |
| 72 | 5.4 | 28.06 | 10.66 | 69.29 |
| 120 | 5.5 | 27.3 | 10.8 | 69.62 |
| Control | 0.4 | 58 | 40 | nd |

TIF and emulsifying activity $E_{24}$ after 24 h with hexadecane.
nd: not detected.

8) Oil recovery in unconsolidated systems (granular).—It consists in using and adding *Serratia marcescens* SmSA tensoactive biomolecules to a granular porous medium with particle sizes ranging from 280 to 540 μm, previously impregnated and saturated with different API gravity oils: from 12 to 25° API. The recovery systems were packed columns with granular rocks. The oil recovery was evaluated volumetrically after the systems were put in contact with the *Serratia marcescens* SmSA tensoactive biomolecules for a time period between 12 and 48 h and temperatures from 30 to 70° C. The biotechnological process of the present invention allows the recovery of a percentage above 16% of residual oil after the secondary recovery process in porous media.

9) Oil recovery in consolidated systems (core).—It consists in preparing a core fragment, measuring porosity and permeability, saturating the core fragment with oil, secondary recovering by waterflooding, enhanced recovering by injection of produced *Serratia marcescens* SmSA tensoactive biomolecules and quantifying the recovered oil. The biotechnological process of the present invention allows the recovery of a percentage above 14% of residual oil after the secondary recovery process in porous media.

EXAMPLES

In this section, some practical Examples from the present invention are described to offer a better understanding of it without limiting its scope.

Example 1

Effect of the Tensoactive Biomolecules of *Serratia Marcescens* SmSA on the Interfacial Tension The interfacial tension was evaluated through the pendant drop method on different systems (Table 8).

TABLE 8

Effect of tensoactive biomolecules by *Serratia marcescens* SmSA on the interfacial tension

| System | Interfacial Tension (mN/m) |
|---|---|
| Oil - water (control) | 25.45 |
| Oil - water - Tensoactive biomolecule | 4.384 |
| Hexadecane - water (control) | 37.9 |
| Hexadecane - water - Tensoactive biomolecule | 1.81 |

The test was carried out by using a oil drop (24° API) and putting it in contact with tensoactive biomolecules by *Serratia marcescens* SmSA. The test was performed at 70° C. The control was an oil-distilled water system. Table 8 shows that tensoactive biomolecules by *Serratia marcescens* SmSA are efficient for reducing the interfacial tension.

Example 2

Enhanced Oil Recovery in Unconsolidated Porous Media (Granular Systems) Using *Serratia Marcescens* (SmSA) Tensoactive Biomolecules The oil recovery was evaluated employing unconsolidated porous systems (granular) with siliciclastic rocks. The rocks were ground, meshed and selected according to particle sizes between 280 and 540 μm. The porous material was previously washed with water and solvents (toluene and chloroform). Afterwards, it was dried in an oven at 60° C. for 48 h.

The systems consisted of glass columns with a length of 20 cm and a diameter of 2.5 cm with a glass jacket through which water was recirculated to control the temperature. The columns were packed with 90 g of granular rock per system. The porous volume of the columns was established.

The rock was impregnated up to saturation with different density oils (from 12 to 25° API) under vacuum conditions. The systems were incubated at 60 and 70° C. These systems were injected with *Serratia marcescens* SmSA tensoactive biomolecules. The injection rate was 5 mL/h and each system (column) was injected with 3-3.75 porous volumes. All the systems were performed in triplicate and with a control, which was injected with water during the recovery test (secondary recovery). The oil percent released by the control was taken away from the volume released by the treatments with the tensoactive biomolecules.

In the tests performed with *Serratia marcescens* SmSA tensoactive biomolecules, the oil recovery was increased from 16.13 to 95.0%.

Example 3

Enhanced Oil Recovery in Consolidated Porous Media (Core) Using Tensoactive Biomolecules from *Serratia Marcescens* SmSA This example consisted in preparing a core fragment, assessing of its porosity and permeability, saturating with oil, secondary recovering by waterflooding, enhanced oil recovering by tensoactive biomolecules from *Serratia marcescens* SmSA and quantifying the oil recovered.

Preparation of the core fragment.—In the oil recovery experimental test, a core fragment of Bedford limestone (lengths from 8 to 20 cm) and oil from a Mexican oil reservoire (12 to 20° API) were used. The core fragment was washed with solvents and dried under vacuum conditions.

The experimental system consisted of a continuous injection pump, an oven for temperature control, transfer cylinders, a differential pressure transducer, a data acquisition system and an experimental cell.

The experimental cell that contained the core was placed inside the oven to control the temperature between 60 and 80° C.; the transfer cylinders were used to displace the fluids (water, oil and tensoactive biomolecules) employing the injection pump; a differential transducer was installed to monitor the pressure drop.

Saturation of the core fragment with distilled water.—It consisted in saturating the core fragment with distilled water using an injection pump to inject different water ratios. The porosity and permeability of the core fragment were measured.

Saturation of the core fragment with oil.—It consisted in injecting oil (from 12 to 20° API) to displace injected water and saturate the core with oil. The oil saturation and the core residual water percentages were determinate. Then, the core was incubated at temperatures from 60 to 80° C. and pressures from 1,137 to 1,706 psi to carry out the recovery process, first by brine injection (secondary recovery) and finally by the injection of *Serratia marcescens* SmSA biomolecules (tertiary or enhanced recovery).

Secondary recovery.—It consisted in injecting brine until oil was no longer recovered from the core. The oil recovery percent due to waterflooding was established.

Tertiary or enhanced recovery.—After the secondary recovery process, a solution of *Serratia marcescens* SmSA tensoactive biomolecules was injected at flow rates from 2.5 to 5 mL/h until completing 4.2 porous volumes; the system was kept at temperatures from 60 to 80° C. *Serratia marcescens* SmSA tensoactive biomolecules reduced the interfacial tension between the oil and water, enhancing the mobilization and recovery of oil. The recovered oil was quantified, obtaining a recovery of 14% of residual oil after the secondary recovery process by effect of the biomolecules from *Serratia marcescens* SmSA. The experimental conditions are summarized in Table 9.

TABLE 9

| Oil recovery conditions | |
|---|---|
| Parameters | Value |
| API gravity, degrees | 12-20 |
| Rock type | Bedford limestone (carbonated) |
| Length, cm | 8-20 |
| Diameter, cm | 2-4 |
| Temperature, ° C. | 60-80 |
| Pressure, Kg/cm$^2$ (psi) | 80-120 (1,137-1,706) |
| Porous volume, cm$^3$ | 15-25 |
| Porosity, % | 15-20 |
| Permeability, mD | 15-50 |
| Floow, mL/h | 2.5-5 |
| Initial oil saturation, % | 50-70 |
| Water saturation, % | 50-30 |
| Oil recovery by waterflooding (secondary), % | 30-40 |
| Oil recovery by tensoactive biomolecule injection, % | 8-10 |
| Recovery of residual oil by tensoactive biomolecule injection, % | 10-15 |
| Total recovery (secondary + biotechnological process), % | 38-50 |

The results obtained through the examples of the present invention show that the *Serratia marcescens* SmSA tensoactive biomolecules are capable of mobilizing and recovering impregnated oil in porous media.

What is claimed is:

1. A biotechnological process for enhancing oil recovery and mobilization of oils contained in porous media, said process comprising the steps of:
   a) obtaining fluid samples and rock samples from the porous media in an oil well, and measuring properties of the fluid sample and rock sample;
   b) obtaining tensoactive biomolecules produced by *Serratia marcescens* SmSA to reduce interfacial tension between oil and water, provide emulsifying activity, said tensoactive biomolecules being active and stable at temperatures of 25 to 120° C., to a concentration of NaCl from 0 to 200,000 ppm, and pressures of 1 to 120 Kg/cm$^2$, wherein said tensoactive biomolecules are obtained by said *Serratia marcescens* SmSA in a culture medium comprising
   2-6 (g/L) Peptone,
   10-15 (g/L) K$_2$HPO$_4$,
   8-18 (g/L) KH$_2$PO$_4$,
   0.5-4.0 (g/L) (NH$_4$)2SO$_4$, and
   5-15 (g/L) soybean oil as a substrate;
   c) injecting the tensoactive biomolecules produced by *Serratia marcescens* SmSA into the porous medium containing the oil; and
   d) recovering said oil from said porous media and well.

2. A biotechnological process according to claim 1, where the oil in the porous media to be recovered has AP/gravities from 12 to 25.

3. A biotechnological process according to claim 1, where the porous media is siliciclastic (sandstone) or carbonate rock.

4. A biotechnological process according to claim 1, where step a) consists of measuring the oil API gravity, the type of porous medium, the porosity and permeability of the porous media, and the temperature, pressure and salinity in the oil well.

5. A biotechnological process according to claim 1, where *Serratia marcescens* SmSA tensoactive biomolecules employed in step c) are stable at, pH from 2 to 12.

6. A biotechnological process according to claim 1, where the tensoactive biomolecules obtained according to step b) are produced at 35° C., aeration of 1,000 mL/min of air, and stirring from 100 to 150 rpm.

7. A biotechnological process according to claim 1, where the tensoactive biomolecules obtained from *Serratia marcescens* SmSA reduce surface tension up to 26 mN/m, a interfacial tension up to 1.8 mN/m with hexadecane and provide emulsifying activity up to 71% with hexadecane, and have dispersing activity measured as oil spreading of 7.1 cm.

8. A biotechnological process according to claim 1, further comprising introducing the tensoactive biomolecules to said well to recover up to 14% of residual oil from the well.

9. A biotechnical process according to claim 1, where the porous media has a porosity equal to or greater than 15%, a permeability of greater than 20 mD, a temperature of up to 120° C., and pressure up to 120 Kg/cm$^2$.

\* \* \* \* \*